(12) United States Patent
Moinet et al.

(10) Patent No.: US 6,437,143 B2
(45) Date of Patent: *Aug. 20, 2002

(54) THIAZOLIDONE-2 DERIVATIVES, 4-DIKETONE SUBSTITUTED, METHOD FOR OBTAINING THEM AND PHARMACEUTICAL COMPOSITONS CONTAINING SAME

(75) Inventors: Gérard Moinet, Orsay; Gérard Botton, Buc; Etienne Prugnard, Paris; Liliane Doare, Chatillon; Micheline Kergoat, Bures sur Yvette; Didier Mesangeau, Combs la ville, all of (FR)

(73) Assignee: Merck Patent Gesellschaft mit beschrankter Haftung (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/202,076

(22) PCT Filed: Jun. 2, 1997

(86) PCT No.: PCT/EP97/02851

§ 371 (c)(1),
(2), (4) Date: Dec. 7, 1998

(87) PCT Pub. No.: WO97/47612

PCT Pub. Date: Dec. 18, 1997

(30) Foreign Application Priority Data

Jun. 7, 1996 (FR) .............................. 96 07070

(51) Int. Cl.⁷ ..................... C07D 277/34; A61K 31/426
(52) U.S. Cl. ....................... 548/183; 548/183
(58) Field of Search ........................ 548/183; 514/369

(56) References Cited

FOREIGN PATENT DOCUMENTS

| EP | 0 008 203 A | 2/1980 |
|----|-------------|--------|
| EP | 0 612 743 A | 8/1994 |
| EP | 0 643 050 A | 3/1995 |
| WO | 96 05186 A  | 2/1996 |

OTHER PUBLICATIONS

Sohda et al., *Chemical and Pharmaceutical Bulletin*, vol. 30, No. 10, pp. 3580–3600 (1982).

*Primary Examiner*—Robert Gerstl
(74) *Attorney, Agent, or Firm*—Millen, White, Zelano & Branigan, P.C.

(57) ABSTRACT

The present invention relates to the field of chemistry and more particularly to that of therapeutic chemistry.

The subject of the present invention is more precisely new 5-phenoxyalkyl-2,4-thiazolidinediones of general formula I:

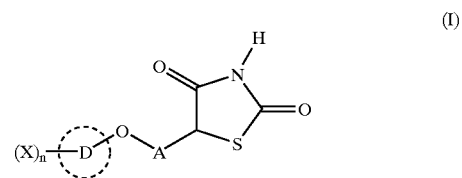

in which

A represents a linear or branched alkylene group comprising from 2 to 16 carbon atoms D represents a homo- or heterocarbon mono-, di- or tricyclic aromatic structure which may include one or more heteroatoms X represents the substituent of the aromatic structure and is as defined in Claim 1 n is an integer ranging from 1 to 3 with the proviso that if A represents a butyl radical,

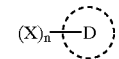

does not represent the 4-chlorophenyl group.

The invention also relates to the tautomeric forms, to the enantiomers, diastereoisomers and epimers of the compounds of general formula I, in free or salified form.

The present invention also relates to the processes for producing the compounds of general formula I, their use as antidiabetic agents, and in the treatment of the metabolic syndrome of insulin resistance, as well as the pharmaceutical compositions which contain the compounds of general formula I.

18 Claims, No Drawings

THIAZOLIDONE-2 DERIVATIVES, 4-DIKETONE SUBSTITUTED, METHOD FOR OBTAINING THEM AND PHARMACEUTICAL COMPOSITONS CONTAINING SAME

The present invention relates to the field of chemistry and more particularly to that of therapeutic chemistry.

More precisely, the subject of the present invention is new 2,4-thiazolidinedione derivatives, namely 5-phenoxyalkyl-2,4-thiazolidinediones, processes for producing them, their use and antidiabetic agents and in the treatment of the metabolic syndrome of insulin resistance, and the pharmaceutical compositions containing them.

Numerous 2,4-thiazolidinedione derivatives have already been described as antidiabetic agents (Takeda, Patent EP 193 256, Sankyo Patent EP 207 581).

The compounds previously described were mainly thiazolidinediones substituted at the 5 position by a benzyl radical, that is to say compounds having an alkylene chain containing only one carbon atom between the thiazolidine ring and an aryl group.

The structure of these compounds comprised in general variations on the substituent carried by the aryl ring of the benzyl radical.

Compounds possessing the structures previously described and exhibiting notable hypoglycaemic and hypotriglyceridaemic activities had as linkage at the 5 position the group R—O—Ar—CH$_2$—.

These variations affected exclusively the R substituent carried by the oxygen at the para position of the phenyl.

Some of these compounds, beside their pharmacological properties, manifest hepatotoxicity phenomena (Takashi Sohda, Chem. Pharm. Bull 30 (1982) 3580).

It is known that, in non-insulin-dependent diabetes, a decrease in the efficacy of insulin leads to hyperglycaemia.

The decrease in the "activity" of insulin is linked, on the one hand, to a pancreatic defect in the insulin response to glucose and, on the other hand, to a hepatic and peripheral (muscles—adipose tissues) insulin resistance.

Some current antidiabetic therapies stimulate mainly insulin secretion, without enhancing insulin resistance, and have as major defect, in the long term, the worsening of the diabetes by depletion of the β-pancreatic cells.

Other antihyperglycaemics such as Metformin and the compounds having the 2,4-thiazolidinedione structure enhance the sensitivity to insulin.

These thiazolidinediones reduce glycemia without stimulating the secretion of insulin and prove more active in insulin resistance with hyperinsulinism.

The compounds of the present invention are new and differ from other 2,4-thiazolidinedione derivatives in properties which the compounds of the prior art did not possess: absence of effect on the secretion of insulin, action on insulin resistance, absence of hepato toxic effect, activity in diabetics in the case of diabetes without hyperinsulinism.

The subject of the present invention is specifically the new 5-phenoxyalkyl-2,4-thiazolidinediones corresponding to the general formula I:

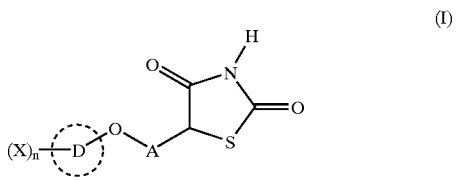

in which
A represents a linear or branched alkylene group comprising from 2 to 16 carbon atoms
D represents a homo- or heterocarbon mono-, di- or tricyclic aromatic structure which may include one or more heteroatoms
X represents a substituent of the aromatic structure, chosen from hydrogen, an alkyl group having from 1 to 6 carbon atoms, an alkoxy group having from 1 to 6 carbon atoms, an alkoxyalkyl group in which the alkoxy and alkyl groups are defined as above, an aryl group defined as an aromatic cyclic structure comprising one or two rings optionally including one or two heteroatoms in the ring such as for example a phenyl or an α- or β-naphthyl, an aralkyl group in which the alkyl group is defined as above and the aryl group is defined as above and optionally comprises one or more substituents, an aralkylaryl group whose aralkyl and aryl fractions are defined as above, a halogen, a trifluoromethyl, a cyano, a hydroxyl, a nitro, an amino, a carboxyl, an alkoxycarbonyl, a carboxamide, a sulfonyl, a sulfone, a sulfonamide, a sulfamoyl, an alkylsulfonylamino, an acylamino, a trifluoromethoxy
n is an integer ranging from 1 to 3 with the proviso that if A represents the butyl radical,

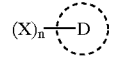

does not represent the 4-chlorophenyl group.

In the preceding text, among the aromatic radicals D, there may be mentioned as homocarbon structure the phenyl, α-naphthyl, β-naphthyl or fluorenyl radical.

Among the heterocyclic aromatic radicals, there may be mentioned pyridyl, the quinolyl ring or carbazolyl.

As regards the invention, an alkyl group is defined as having from 1 to 6 carbon atoms and especially a methyl, ethyl, propyl, isopropy, butyl, isobutyl, tert-butyl or pentyl radical and the like, an alkoxy group is defined as having from 1 to 6 carbon atoms and especially a methoxy, ethoxy, propoxy, isopropoxy, butoxy or isobutoxy radical and the like, a halogen group is defined as being fluorine, chlorine, bromine or iodine.

The alkylene chain A is a linear or branched hydrocarbon chain having from 2 to 16 carbon atoms, which is saturated or has one or more ethylene bonds, optionally substituted with a hydroxyl radical or with a phenyl radical. An example of such a chain will be an ethylene or propylene radical.

The present invention also relates to tautomeric forms of the compounds of general formula I, to the enantiomers, diastereoisomers and epimers of these compounds, as well as their solvates.

It can be envisaged that the ketone functions carried by the thiazolidine ring may become enolized and give rise to monoenols.

The thiazolidinedione derivatives of general formula I which possess an acidic proton on the nitrogen of the thiazolidinedione ring may, in this case, be salified and exist in the form of basic salts.

Examples of basic salts of the compounds of general formula I include the pharmacologically acceptable salts, such as the sodium salts, potassium salts, magnesium salts, calcium salts, amine salts and other salts of the same type (aluminium, iron, bismuth and the like). The amine salts which are not pharmacologically acceptable may serve as means for identification, purification or resolution.

Among the compounds of general formula I according to the invention, there may be mentioned more particularly, as compounds currently preferred:

5-[3-(4-fluorophenoxy)propyl]-2,4-thiazolidinedione
5-(2-phenoxyethyl)-2,4-thiazolidinedione
5-[2-(4-fluorophenoxy)ethyl]-2,4-thiazolidinedione
5-{[1-hydroxy-2-(4-fluorophenoxy)]ethyl}-2,4-thiazolidinedione
5-{[2-hydroxy-3-(4-fluorophenoxy)]propyl}-2,4-thiazolidinedione
5-[1-methyl-2-phenoxyethyl]-2,4-thiazolidinedione
5-[2-(4-cyanophenoxy)ethyl]-2,4-thiazolidinedione
5-[2-(2-fluorophenoxy)ethyl]-2,4-thiazolidinedione
5-[2-(2-naphthyloxy)ethyl]-2,4-thiazolidinedione and their pharmacologically acceptable salts.

The invention also relates to the processes for producing the 5-phenoxyalkyl-2,4-thiazolidinedione of general formula I.

A process of synthesis according to the invention, (route A), is a malonic synthesis, which consists in that a compound of formula II:

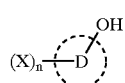

(II)

in which X, D and n are defined as above,
is subjected to the action of a dihaloalkyl of formula III:

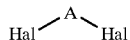

(III)

in which

Hal represents a chlorine or bromine atom,

A is an alkylene radical defined as above, in the presence of a basic agent, to form a compound of general formula IV:

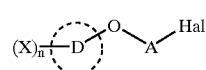

(IV)

in which X, D, n and A are defined as above,
which is subjected to the action of a dialkyl malonate of formula V:

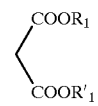

(V)

in which $R_1$ and $R'_1$ are alkyl radicals,
in the presence of an alkali metal alcoholate, to form a compound of general formula VI:

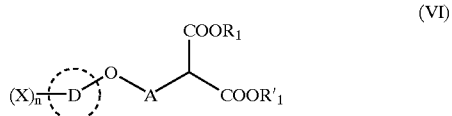

(VI)

in which X, D, n, A, $R_1$ and $R'_1$ are defined as above, which is subjected to halogenation by the action of a halogenating agent to form the compound of general formula VII:

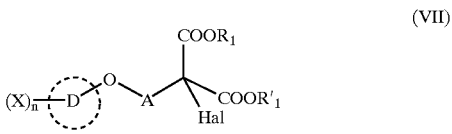

(VII)

in which

Hal represents a chlorine or bromine atom,

X, D, n, A, $R_1$ and $R'_1$ are defined as above.

The malonic compound VI may be halogenated with an N-haloamide or an N-haloimide after formation of the anion, as for example by the action of sodium hydride in tetrahydrofuran.

The dialkyl diester of general formula VII is decarboxylated and saponified by heating in an acidic mixture consisting especially of hydrochloric acid and acetic acid to give the α-haloacid of general formula VIII:

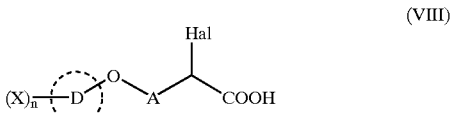

(VIII)

in which Hal, X, D, n and A are defined as above,
which is reacted with thiourea to form a 2-imino-4-thiazolidinone of general formula IX:

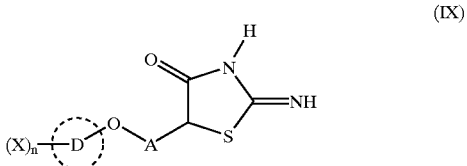

(IX)

in which the X, D, n and A groups are defined as above, which, without being necessarily isolated, is hydrolysed to a 2,4-thiazolidinedione of general formula I by adding an acidic mixture such as hydrochloric acid.

This hydrolysate is preferably carried out by heating under reflux.

In this process, the basic agent used to form the compound of general formula IV is preferably an alkali metal hydroxide and especially sodium hydroxide. Likewise, the haloamide may be N-chloroacetamide, N-bromoacetamide or N-bromobenzamide and the haloimide may be N-chlorosuccinimide or N-chlorophthalimide.

Another process of synthesis by the malonic route (route B) consists in subjecting a compound of formula X:

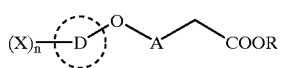

(X)

in which

R represents an alkyl group,

X, D, n and A are as defined above, to halogenation to form the α-halogenated ester of general formula XI:

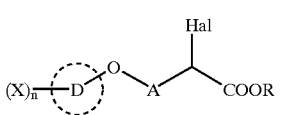

(XI)

in which

Hal represents a chlorine or bromine atom,

X, D, n and A are defined as above, and then in reacting the latter with thiourea in the presence of a buffering agent such as sodium acetate to form the 2-imino-4-thiazolidinone of formula IX:

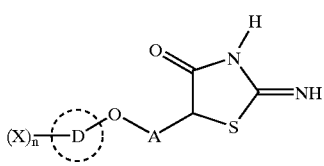

(IX)

in which X, D, n and A are as defined above, which is hydrolysed by heating under reflux in hydrochloric acid, to form the thiazolidinedione of general formula I:

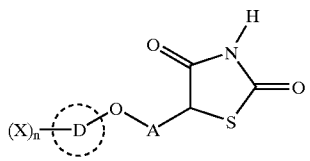

(I)

in which

D represents a homo- or heterocarbon, mono-, di- or tricyclic aromatic structure which may include one or more heteroatoms, X represents a substituent of the aromatic structure and is defined as above, A represents a linear or branched alkylene group comprising from 2 to 16 carbon atoms.

Another process of synthesis, according to the invention (route C), consists in that a halogenated compound of formula IV:

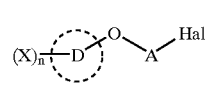

(IV)

in which

Hal represents a chlorine or bromine atom,

X, D, n and A are defined as above, is subjected to the action of the 2,4-thiazolidinedione dianion obtained by the action of an alkali metal derivative such as butyllithium on 2,4-thiazolidinedione to form a compound of general formula I.

In another process according to the invention (route D), the synthesis starts with an aryloxyalkyl aldehyde and consists in subjecting the aldehyde compound of formula XII:

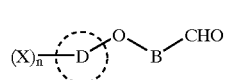

(XII)

in which

B represents a linear or branched alkylene group, comprising from 1 to 15 carbon atoms X, D and n are as defined above, to the action of the 2,4-thiazolidinedione dianon obtained by the action of an alkali metal derivative on 2,4-thiazolidinedione, to form a compound of general formula XIII:

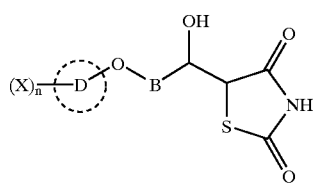

(XIII)

in which B, X, D and n are as defined above.

This compound is then converted to a dehydroxylated compound of formula I, by dehydration and then selective hydrogenation, or alternatively by reduction of the alcohol function to a saturated derivative.

The invention also relates to another process for preparing the compounds of general formula I (route E), in which an oxirane of formula XIV:

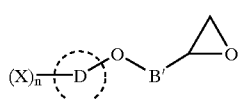

(XIV)

in which

B' represents a linear or branched alkylene group comprising from 1 to 14 carbon atoms, X, D and n are defined as above, formed by reaction of an epihalohydrin on an aromatic derivative with [sic] the 2,4-thiazolidonedione dianion obtained by the action of a strong base such as butyllithium to form the compound of general formula XV:

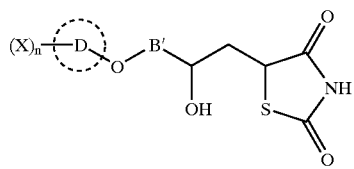

(XV)

in which X, D, n and B' are defined as above.

The compound of formula XV is then converted to a dehydroxylated compound of general formula I by dehydration and hydrogenation.

Another process for producing the compounds of general formula I (route F) consists, starting with a ketone, in subjecting the said ketone of general formula XVI:

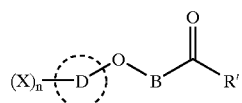

(XVI)

in which
R' represents a linear or branched alkyl group, or an aryl or aralkyl group, substituted or not,
X, D, n and B are defined as above,
to the action of 2,4-thiazolidinedione in the presence of an organic base to form, after dehydration of the intermediate carbinol in an acidic medium, the compound of general formula XVII:

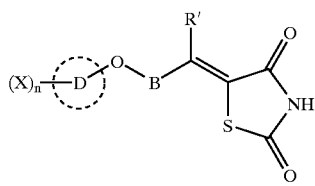

(XVII)

in which X, D, n, B and R' are defined as above,
and then in reducing the double bond by hydrogenation in the presence of a catalyst, to form the compound of general formula I, in which the alkylene chain is a branched chain:

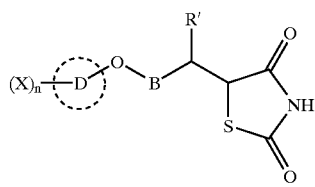

(I)

X, D, n, B and R' are defined as above.

The catalytic hydrogenation of the compound XVII is carried out preferably in the presence of a metal of the platinum family on an inert support such as, for example, palladized charcoal, platinized charcoal or palladium on calcium carbonate.

To summarize, in the processes of synthesis C, D, E and F, the compounds of general formula I are obtained by the action of various electrophilic agents as described below, in a non-limiting manner on the 2,4-thiazolidinedione dianion, preferably at low temperature.

This dianion may be obtained by the action of a strong base such as lithium diethylamide, lithium amide, lithium diisopropylamide, n-BuLi, on 2,4-thiazolidinedione.

| Route of synthesis | Electrophilies |
|---|---|
| Route C | 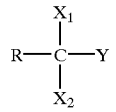 |
| Route D | R—CHO |
| Route E | 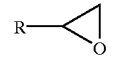 |
| Route F | 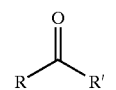 |

R represents:

(X)$_n$—D—O—B— or (X)$_n$—D—O—B'—

D is defined as above,
X represents the substituent of the aromatic structure and is defined as above,
B represents a linear or branched alkylene group comprising from 1 to 15 carbon atoms,
B' represents a linear or branched alkylene group comprising from 1 to 14 carbon atoms,
Y represents a bromine or chlorine atom or a methylsulfonyloxy or p-toluenesulfonyloxy radical,
R' represents a linear or branched alkyl group, or alternatively R' represents an aryl or aralkyl group, substituted or not,
$X_1$ represents a hydrogen or a linear or branched alkyl group,
or alternatively $X_1$ represents an aryl or aralkyl group, substituted or not,
$X_2$ represents a hydrogen or a linear or branched alkyl group,
or alternatively $X_2$ represents an aryl or aralkyl group, substituted or not.

The invention also comprises, as new products, the intermediate compounds formed during the various processes of synthesis and especially the compounds of general formula: VII, VIII, IX, XIII, XV and XVII.

The compounds according to the invention manifest very valuable pharmacological properties and, as a result, find use in therapy.

The compounds of the invention differ from the other 2,4-thiazolidinedione derivatives in the intensity of their antidiabetic activity in models of diabetes without hyperinsulinism where the prior art compounds, such as for example troglitazone, prove to be little active.

Thus, the compounds of the invention can be used in the treatment of non-insulinopenic diabetic states, making it possible to obtain a better control of glycemia by having a reduced circulating insulin level.

The prevention of this relative hyperinsulinism, associated with an improvement of dyslipidaemias and an antioxidant activity, may contribute to a reduction in the micro- and macroangiopathic risks.

The compounds of the invention can be used in the treatment of the metabolic syndrome of insulin resistance involving a beneficial therapeutic effect on non-insulin-dependent diabetes, hypoinsulinism, hypertension and dyslipidaemias—but also in non-insulin-dependent diabetes with hyperinsulinism.

The compounds find, furthermore, use in the treatment of hypertension in insulin resistant subjects, associated or otherwise with other metabolic abnormalities.

The diuretic activity and the reduction in the $Ca^{2+}$ capture observed on rat aorta can cause an antihypertensive activity for some of the compounds of general formula I.

Some of the compounds possess, in addition, antiradical activities towards the hydroxyl and superoxide anion, demonstrated with the aid of a so-called cellular investigation model.

For these purposes, the compounds according to the invention are used in the form of pharmaceutical compositions which contain, as active ingredient, at least one compound of general formula I, in combination or mixed with a pharmaceutically acceptable non-toxic inert excipient or vehicle.

The pharmaceutical compositions according to the invention are intended for administration by the parenteral, digestive, rectal, permucosal or percutaneous route.

They will therefore be presented in the form of injectable solutions or suspensions or multi-dose vials, in the form of plain or coated tablets, sugar-coated tablets, capsules, gelatin capsules, pills, cachets, powders, suppositories or rectal capsules, solutions or suspensions, for percutaneous use in a polar solvent, or for permucosal use.

Suitable excipients are cellulose derivatives or microcrystalline cellulose, alkaline-earth metal carbonates, magnesium phosphate, starches, modified starches or lactose for the solid forms.

For rectal use, cocoa butter or polyethyleneglycol stearates are the preferred excipients.

For parenteral use, water, aqueous solutions, physiological saline, isotonic solutions are the vehicles most conveniently used.

The dosage may vary within wide limits according to the therapeutic indication and the route of administration, as well as the age and weight of the subject.

As a general rule, the unit dosage can range from 1 to 200 mg per dose and the daily dosage can range from 2 to 500 mg.

The following examples illustrate the invention without however limiting it.

EXAMPLE 1

5-[3-(4-fluorophenoxy)propyl]-2,4-thiazolidinedione
(I) (According to Route A)

Stage A

Preparation of 1-(3-bromopropoxy)-
4-fluorobenzene (IV)

A mixture of 58.9 g of 4-fluorophenol, 137 g of 1,3-dibromopropane and 65 ml of water is heated to 60° C. 58 ml of a 10 N sodium hydroxide solution are then added and the mixture is heated under reflux for 72 h, with stirring. The reaction medium is added to 500 ml of water and 500 ml of dichloromethane. The organic phase is decanted, washed 3 times with water, dried over sodium sulfate and concentrated under a strong vacuum, to give 120 g of an oil which is purified on a silica column, eluting with petroleum ether. 67.5 g of 1-(3-bromopropoxy)-4-fluorobenzene are obtained in the form of an oil.

NMR: ($CDCl_3$) δ ppm 2.25 (2H, m, $CH_2$); 3.55 (2H, t, $CH_2Br$); 4.05 (2H, t, $CH_2O$), 6.7–6.9 (4H, m, phenyl protons)

Stage B

Preparation of the ethyl diester of [3-(4-fluorophenoxy)propyl]propanedioic acid (VI)

A sodium ethoxide solution (2.68 N in ethanol) is heated to 50° C. and 35 ml of diethyl malonate are added dropwise. The mixture is stirred for 20 min, then 53.6 g of 1-(3-bromopropoxy)-4-fluorobenzene are added. The mixture is then heated under reflux for 2 h.

The reaction medium is concentrated under vacuum and the residue is taken up in 500 ml of ethyl acetate and 500 ml of water. The organic phase is washed with water, dried over sodium sulfate and concentrated under a strong vacuum.

67.5 g of ethyl diester of [3-(4-fluorophenoxy)propyl]propanedioic acid are obtained in the form of an oil, which oil is used without further purification during the next stage:

IR: 1731 $cm^{-1}$ (C=O ester)

NMR: ($CDCl_3$) δ ppm 1.2 (6H, t, 2 $CH_3$); 1.4–2.2 (4H, m, 2 $CH_2$); 3.3 (1H, m, CH); 3.7–4.3 (6H, m, 2 $CH_2O$+$CH_2$—O—Ar)

Stage C

Preparation of the ethyl diester of chloro-[3-(4-fluorophenoxy)propyl]propanedioic acid (VII)

Under an inert atmosphere, 7.4 g of sodium hydride (80% in suspension in oil) are added, in small fractions, to 70.3 g of the ethyl diester of [3-(4-fluorophenoxy)propyl]propanedioic acid in 500 ml of anhydrous tetrahydrofuran.

The reaction is exothermic.

The reaction medium is added [sic] for 1 h after it has returned to room temperature and 33 g of N-chlorosuccinimide are added in fractions. The reaction is slightly exothermic.

The mixture is then stirred for 20 h at 20° C. 500 ml of water and 600 ml of ethyl acetate are added to the reaction medium. The organic phase is decanted and washed with 3 times 400 ml of water.

The organic phase is then dried over sodium sulfate, evaporated under vacuum to give 71 g (yield: 91%) of the ethyl diester of chloro-[3-(4-fluorophenoxy)propyl]propanedioic acid in the form of an oil which is used without further purification during the next stage.

IR: 1747 $cm^{-1}$ (C=O ester)

NMR (DMSO) δ ppm 1.2 (6H, t, 2 $CH_3$—$CH_2$), 1.75 (2H, m, $CH_2$), 2.3 (2H, m, $CH_2$), 4(6H, m, $CH_2$ esters+$CH_2$)

Stage D

Preparation of 2-chloro-5-(4-fluorophenoxy)
pentanoic acid (VIII)

70 g of the ethyl diester of chloro-[3-(4-fluorophenoxy)propyl]propanedioic acid in a mixture of 200 ml of 6 N hydrochloric acid and 200 ml of glacial acetic acid are heated under reflux for 20 h.

600 ml of water and 400 ml of ethyl acetate are then added. The organic phase is washed 5 times with 500 ml of water, dried over sodium sulfate and then evaporated to give 56 g of 2-chloro-5-(4-fluorophenoxy)pentanoic acid in the form of an oil which is used without further purification.

NMR: (DMSO) δ ppm 1.4–2.3 (4H, m, 2 CH$_2$); 3.9 (2H, t, CH$_2$—O); 4.6 (1H, t, CH); 6.8–7, (4H, m, phenyl protons)

Stage E

Preparation of 5-[3-(4-fluorophenoxy)propyl]-2,4-thiazolidinedione (I)

56 g of 2-chloro-5-[4-fluorophenoxy)]pentanoic acid and 23 g of thiourea in 410 ml of 2-methoxyethanol are heated at 110° C. for 3 h. 410 ml of 2 N hydrochloric acid are then added and the mixture is heated under reflux for 20 h. After returning to room temperature, 500 ml of water and 500 ml of ethyl acetate are added.

The organic phase is decanted and washed with 3 times 400 ml of water. The organic phase is dried over sodium sulfate and then evaporated under vacuum. 48 g of oil are obtained, which oil is purified on silica, eluting with a dichloromethane/acetone (97/3 by volume) mixture.

21 g of solid are obtained which are recrystallized from a dichloromethane/heptane mixture. 13 g of 5-[3-(4-fluorophenoxy)propyl]-2,4-thiazolidinedione are thus obtained in the form of a white solid whose melting point is 119–121° C.

EXAMPLE II 5-(2-phenoxyethyl)-2,4-thiazolidinedione (I)
(According to Route B)

Stage A

Preparation of 2-imino-5-(2-phenoxyethyl)-4-thiazolidinone (IX)

18.5 g of the ethyl ester of 2-bromo-4-phenoxy-butanoic acid, 6 g of thiourea and 5 g of sodium acetate in 100 ml of 2-methoxyethanol are heated under reflux for 3 h. The reaction medium is cooled and concentrated under vacuum and the residue obtained is taken up in 75 ml of demineralized water and 75 ml of dichloromethane.

The organic phase is decanted, washed and dried over sodium sulfate to give an oil. By crystallizing from acetonitrile, this oil gives 6 g of 2-imino-5-(2-phenoxyethyl)-4-thiazolidinone in the form of a solid which decomposes above 250° C.

Stage B

Preparation of 5-(2-phenoxyethyl)-2,4-thiazolidinedione (I)

6 g of 2-imino-5-(2-phenoxyethyl)-4-thiazolidinone in 100 ml of 2 N hydrochloric acid are heated under reflux for 8 h. A solid crystallizes. This solid is filtered and washed with water and then purified by recrystallization from a cyclohexane/ethyl acetate mixture to give 3 g of 5-(2-phenoxyethyl)-2,4-thiazolidinedione hemihydrate, melting at 105–107° C.

5-(2-Phenoxyethyl)-2,4-thiazolidinedione was also obtained by the process of synthesis according to route C. This compound is obtained in the anhydrous form and then melts at 81–83° C.

EXAMPLE III

5-[2-(4-fluorophenoxy)ethyl]-2,4-thiazolidinedione (I) (According to Route C)

33.4 g of 2,4-thiazolidinedione are dissolved in 1700 ml of tetrahydrofuran, under an inert atmosphere, and while the temperature of the reaction medium is maintained at −78° C., 228 ml of butyllithium (2.5 M hexane) are added dropwise. The temperature is allowed to rise to 20° C. and the mixture is stirred for 2 h at this temperature. It is cooled to −78° C. and 31.2 g of 1-(2-bromoethoxy)-4-fluorobenzene in solution in 600 ml of tetrahydrofuran are added dropwise. The temperature is then allowed to rise to room temperature and the mixture is stirred for 20 h at this temperature. The reaction medium is poured over 2300 ml of 2 N hydrochloric acid.

The organic phase is decanted and concentrated. The residue is taken up in 800 ml of ethyl acetate and 1000 ml of water. The organic phase is decanted, washed 4 times with water, dried over sodium sulfate and evaporated to give an oil which is purifed on silica, eluting with a dichloromethane/acetone (97/3 by volume) mixture. The product obtained is recrystallized from diisopropyl ether. 8.5 g of 5-[2-(4-fluorophenoxy)ethyl]-2,4-thiazolidinedione are obtained in the form of a white solid whose melting point is 94–96° C.

EXAMPLE IV

5-{[1-hydroxy-2-(4-fluorophenoxy)]ethyl}-2,4-thiazolidinedione (XIII) (According to Route D)

Stage A

Preparation of 4-fluorophenoxyacetaldehyde (XII)

42.9 g of sodium tert-butoxide are added to 50 g of 4-fluorophenol in solution in 180 ml of tert-butanol, followed by 53 ml of bromoacetaldehyde dimethyl acetal and the reaction medium is heated under reflux for 96 h under an inert atmosphere.

It is concentrated under vacuum and the residue is taken up in ethyl ether. The organic phase is washed with water and then with a 2 N aqueous sodium hydroxide solution until the starting phenol completely disappears. The organic phase is again washed with water and then dried over sodium sulfate and then concentrated under vacuum. The residue is solubilized in a mixture of 1000 ml of THF and 700 ml of 5% aqueous hydrochloric acid, and then heated under reflux for 3 h.

After cooling, 500 ml of water and 500 ml of ethyl acetate are added to the reaction medium. The organic phase is decanted, dried over sodium sulfate and concentrated under vacuum to give an oil which is purified on a silica column, eluting with dichloromethane. 36 g of 4-fluorophenoxyacetaldehyde are obtained in the form of an oil which is used without further purification.

IR: 1739 cm$^{-1}$ (C=O)

NMR (CCl$_4$) δ ppm 4.35 (2H, d, CH$_2$), 6.4–7.1 (4H, m, phenyl protons), 9.8 (1H, t, CHO)

These data are identical to those described in the literature (J. Med. Chem. 1977, 20, No. 4, p. 540–6).

Stage B

Production of 5-{[1-hydroxy-2-(4-(fluorophenoxy)]ethyl}-2,4-thiazolidinedione (XIII)

Under an inert atmosphere, a solution of 13.7 g of 2,4-thiazolidinedione in 200 ml of anhydrous tetrahydrofuran is prepared. 94 ml of butyllithium (2.5 M in hexane) are added dropwise at −78° C.

The reaction medium is then stirred for 3 h at 20° C. and then again cooled to −78° C. and 36 g of 4-fluorophenoxyacetaldehyde in solution in 40 ml of anhydrous tetrahydrofuran are added gently. The mixture is stirred for 30 min at −78° C. and then for 20 h at room temperature. The reaction medium is taken up in 250 ml of an ice/1 N hydrochloric acid mixture. The organic phase is decanted, concentrated under vacuum and taken up in 400 ml of ethyl acetate and 400 ml of water.

The organic phase is washed with water, dried over sodium sulfate and then evaporated under vacuum to give an oil which is purified on a silica column, eluting with a dichloromethane/acetone (90/10 by volume) mixture. 12.2 g of an oil are obtained, which oil crystallizes. The solid obtained is recrystallized from a dichloromethane/heptane mixture to give 7.6 g of 5-{[1-hydroxy-2-(4-(fluorophenoxy)]ethyl}-2,4-thiazolidinedione in the form of a white solid whose melting point is 131–133° C.

EXAMPLE V

5-{[2-hydroxy-3-(4-(fluorophenoxy)]propyl}-2,4-thiazolidinedione (XV) (According to Route E)

Stage A

Preparation of (4-fluorophenoxy) methyloxirane (XIV)

45 g of 4-fluorophenol, 94 ml of epichlorohydrin and 56 g of potassium carbonate in 800 ml of anhydrous acetonitrile are heated under reflux for 20 h, under an inert atmosphere. 400 ml of water and 200 ml of ethyl acetate are added to the reaction medium.

The organic phase is decanted, washed twice with water, dried over sodium sulfate and concentrated under vacuum. The residue is purified on a silica column, eluting with a dichloromethane/heptane (50/50 by volume) mixture, to give 40 g of (4-fluorophenoxy)methyl oxirane in the form of an oil which is used in the next stage without further purification.

NMR (DMSO) δ ppm 2.8 (2H, m, $CH_2$), 3.3 (1H, m, CH) 3.8 (1H, dd, $CH_2$), 4.3 (1H, dd, $CH_2$), 6.7–7.3 (4H, m, phenyl protons)

These data are identical to those described in the literature (J. Med. Chem. 1978, 21, No. 10, p. 1073–6).

Stage B

Production of 5-{[2-hydroxy-3-(4-(fluorophenoxy)] propyl}-2,4-thiazolidinedione (XV)

A solution of 28 g of 2,4-thiazolidinedione in 450 ml of anhydrous tetrahydrofuran is prepared under an inert atmosphere. 191 ml of butyllithium (2.5 M in hexane) are added dropwise at −78° C. The reaction medium is then stirred for 3 h at 20° C. and then cooled again to −78° C. and 40 g of (4-fluorophenoxy)methyloxirane in solution in 150 ml of anhydrous tetrahydrofuran are added gently. The mixture is stirred for 30 min at −78° C. and then for 20 h at room temperature.

The reaction medium is taken up in 600 ml of an ice/1 N hydrochloric acid mixture. The organic phase is decanted and concentrated under vacuum. The residue is taken up in ethyl acetate and the solution obtained is washed several times with water, dried over sodium sulfate and then concentrated under vacuum. The residue is purified on a silica column, eluting with a dichloromethane/acetone (90/10 by volume) mixture to give 15.2 g of an oil which crystallizes.

This solid is recrystallized from a dichloromethane/heptane mixture to give 10.5 g of 5-{[2-hydroxy-3-(4-fluorophenoxy)]propyl}-2,4-thiazolidinedione in the form of a white solid whose melting point is 96–98° C.

EXAMPLE VI

5-[1-methyl-2-phenoxymethyl]-2,4-thiazolidinedione (I) (According to Route F)

Stage A

Preparation of 5-[1-methyl-2-phenoxyethylidene]-2,4-thiazolidinedione (XVII)

29.3 g of 2,4-thiazolidinedione and 34.2 ml of phenoxy-2-propanone are heated under reflux in 500 ml of toluene for 20 h in the presence of 2.5 ml of piperidine and 1.3 l of acetic acid.

4.75 g of paratoluenesulfonic acid monohydrate are added and the mixture is again heated under reflux for 20 h, removing the water formed with the aid of a Dean-Stark apparatus. 1000 ml of water are then added. The organic phase is decanted, washed twice with water, dried over sodium sulfate and evaporated. The residue is purified on a silica column, eluting with a dichloromethane/acetone (90/10 by volume) mixture. The solid is taken up in diisopropyl ether and gives, after filtration, 17 g of 5-[1-methyl-2-phenoxyethylidene]-2,4-thiazolidinedione in the form of a yellow solid whose melting point is 153–155° C.

Stage B

Production of 5-[1-methyl-2-phenoxyethyl]-2,4-thiazolidinedione (I)

9 g of 5-[1-methyl-2-phenoxyethylidene]-2,4-thiazolidinedione are hydrogenated at 100° C. at a pressure of 40–50 bar, for 100 h in dioxane, in the presence of 9 g of 10% palladized charcoal.

The reaction medium is filtered on Celite and evaporated under vacuum to give 5.5 [lacuna] of 5-[1-methyl-2-phenoxyethyl]-2,4-thiazolidinedione whose melting point is 106–108° C.

EXAMPLE VII

Pharmacological Study of the Compounds of the Invention

1—Aim of the Experiment

To determine an antidiabetic activity by the oral route on an experimental model of non-insulin-dependent diabetes induced in rats by Streptozotocin.

2—Procedure

Method for Obtaining the Rat nOSTZ Model

The non-insulin-dependent diabetes model is obtained in rats by a neonatal injection (on the day of birth) of Streptozotocin.

The diabetic rats used are 8 weeks old.

The animals are kept, from the day of their birth to the day of the experiment, in an animal house at a regulated temperature of 21 to 22° C., and subjected to a fixed cycle of light (from 7.00 h to 19.00 h) and of darkness (from 19.00 h to 7.00 h). Their diet consisted of a maintenance diet; water and food were provided "ad libitum", with the exception of the 2 hours of fasting preceding the tests where food is withdrawn.

Method

On the day of the experiment, the rats are treated orally with the test product, and then 90' later, are anaesthetized with Nembutal. 2 hours after the administration of the product, a 500-µl blood sample is collected from the tail.

Collection of the Samples

The blood is collected over Heparin. All the tubes are placed on ice at the time the samples are collected. These are then centrifuged for 10 minutes at 3000 revolutions/minute to separate the organized elements as rapidly as possible.

The plasma obtained is distributed into 2 aliquots:
one for the assay of glycaemia and lactatamia; these assays are carried out immediately
the other for the assay of insulinaemia—is stored in the freezer at −20° C. up to the day of the assay
Analytical Procedure
Glucose and Lactate
They are determined by the glucose oxydase and lactate oxydase technique (Eppendorf Ebio 6666)
Insulin
The plasma insulin is assayed by a radio-immunological method
3—Results
Table 1 collates the main results obtained.

TABLE I

| COMPOUND | 20 mg/kg/4d | | 200 mg/kg/4d | |
|---|---|---|---|---|
| | % Glycaemia | % Insulinaemia | % Glycaemia | % Insulinaemia |
| 1 | −15 | | −26 | |
| 2 | −2 | −1 | −19 | −27 |
| 3 | −17 | +1 | −17 | −37 |
| 4 | −3 | −35 | −17 | −33 |
| 5 | −10 | −9 | −23 | −62 |
| 6 | −20 | 0 | −26 | −49 |
| 7 | +1 | +6 | −10 | −47 |
| 8 | −3 | −30 | −9 | −26 |
| 9 | 10 | −15 | −16 | −30 |
| 10 | −1 | −12 | −9 | −48 |
| 11 | −12 | −31 | −21 | −23 |
| 12 | −6 | −35 | −6 | −56 |
| 13 | −14 | | −2 | |
| 14 | −4 | −23 | −7 | −51 |
| 15 | −14 | −9 | −22 | −12 |
| 16 | −6 | −12 | −22 | 0 |
| 17 | −20 | +4 | −7 | −5 |
| 18 | −8 | −4 | −9 | −17 |
| 19 | −6 | +2 | −20 | −10 |
| 20 | −10 | | −14 | |
| 21 | −1 | | −9 | |

These results show the efficacy of the compounds according to the invention in reducing spontaneous glycaemia and the circulating insulin level in animals made diabetic.
PPARγ's The thiazolidinedione derivatives are antidiabetic agents which increase the insulin sensitivity of the target tissues in animal models of non-insulin-dependent diabetes. Thiazolidinediones are known to promote in vitro the differentiation, into adipocytes, of the preadipocyte and mesenchymateuse cell lines; however, the molecular base of this adipogenic effect remains uncertain. The thiazolidinediones are potent and selective activators of the γ receptor activated by a peroxisome proliferator (=PPARγ: "Peroxisome Proliferator—actived Receptor γ"), a member of the "super" family of nuclear receptors whose action in adipogenesis has recently been demonstrated. The most potent of these agents, thiazolidinedione BRL 49653, binds to PPARγ with a dissociation constant Kd approximately equal to 40 nM. The result of the treatment of the cell line C3H10T1/2 with BRL 49653 is an effective differentiation into adipocytes. This demonstrates the high affinity of the PPAR ligand and proves that PPARγ is a molecular target for the adipogenic effects of thiazolidinediones.

Unlike the other known thiazolidinediones (troglitazone, proglitazone, BRL 49653), the thiazolidinediones of the present invention have no activity on the transactivation of PPARγ. Likewise, the thiazolidinediones of the present invention have no activity on the transactivation of the other nuclear receptors PPARs, PPARα, and PPARδ. The thiazolidinediones of the present invention are weakly or not adipogenic on the 3T3-L1 cells, unlike the prior art thiazolidinediones which promote the differentiation of the 3T3-L1 cells into adipocytes.

Thus, the compounds of the present invention have properties which the prior art compounds did not possess.

EXAMPLE VIII

The following compounds corresponding to the general formual I were prepared by one of the methods of synthesis A, B, C, D, E or F. Their constants are listed in Table II below.

TABLE II

| Compound | STRUCTURE | m.p. in ° C. (Köfler) | calculated C H N | found C H N | Route of synthesis |
|---|---|---|---|---|---|
| 1 | 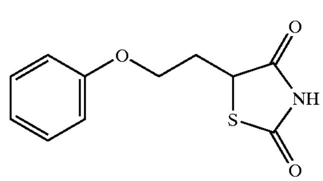 | 81–83 anhydrous 105–107 hemi hydrate | 55.88 4.67 5.90 | 55.60 4.68 5.85 | B, C |
| 2 | 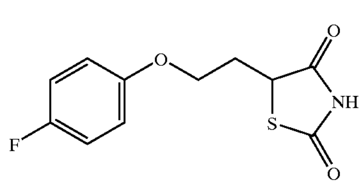 | 94–96 | 51.76 3.95 5.49 | 51.70 4.06 5.46 | A, C |

TABLE II-continued

| Compound | STRUCTURE | m.p. in °C. (Köfler) | calculated C H N | found C H N | Route of synthesis |
|---|---|---|---|---|---|
| 3 | 4-F-C6H4-O-(CH2)3-thiazolidine-2,4-dione | 121–123 | 53.52 4.49 5.20 | 53.42 4.60 5.15 | A |
| 4 | 4-Cl-C6H4-O-(CH2)2-thiazolidine-2,4-dione | 116–118 | 48.62 3.71 5.15 | 48.51 3.85 5.14 | C |
| 5 | 4-Br-C6H4-O-(CH2)2-thiazolidine-2,4-dione | 104–106 | 41.79 3.19 4.43 | 41.79 3.25 4.42 | C |
| 6 | 4-NC-C6H4-O-(CH2)2-thiazolidine-2,4-dione | 149–151 | 54.95 3.84 10.68 | 54.88 3.92 0.59 | C |
| 7 | benzo[1,4]dioxin-2-ylmethyl-thiazolidine-2,4-dione | 145 | 54.33 4.18 5.28 | 54.32 4.28 5.21 | A |
| 8 | 4-CH3-C6H4-O-(CH2)2-thiazolidine-2,4-dione | 119–121 | 57.35 5.21 5.57 | 57.16 5.33 5.49 | C |
| 9 | 4-Cl-C6H4-O-(CH2)5-thiazolidine-2,4-dione | 68–70 | 54.96 5.53 4.27 | 54.82 5.55 4.20 | A |
| 10 | 4-F-C6H4-O-(CH2)4-thiazolidine-2,4-dione | 98–100 | 56.55 5.42 4.71 | 56.59 5.58 4.67 | A |

TABLE II-continued
| Compound | STRUCTURE | m.p. in °C. (Köfler) | calculated C H N | found C H N | Route of synthesis |
|---|---|---|---|---|---|
| 11 | 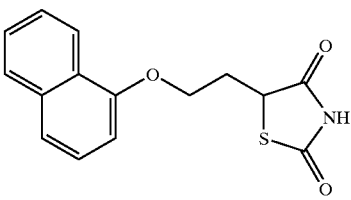 | 185–187 | 62.70 4.56 4.87 | 62.58 4.61 4.79 | C |
| 12 | 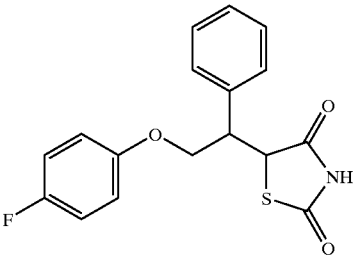 | 121 | 61.62 4.26 4.23 | 61.71 4.44 4.22 | C |
| 13 | 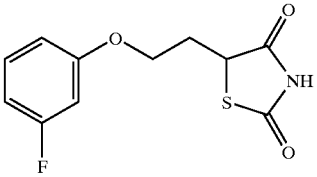 | 87 | 51.76 3.95 5.49 | 51.60 3.97 5.51 | C |
| 14 | 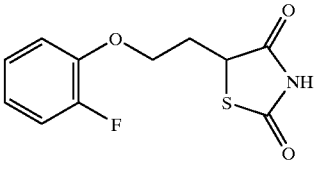 | 138 | 51.76 3.95 5.49 | 51.65 4.06 5.51 | C |
| 15 | 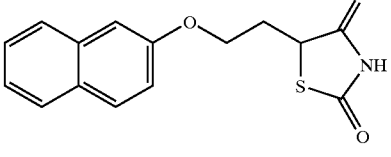 | 133 | 62.70 4.56 4.87 | 62.81 4.68 4.91 | C |
| 16 | 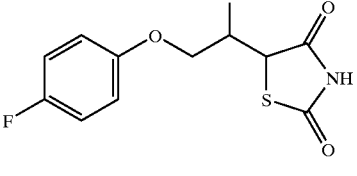 | 131–133 | 48.70 3.71 5.16 | 48.61 3.79 5.12 | D |
| 17 | 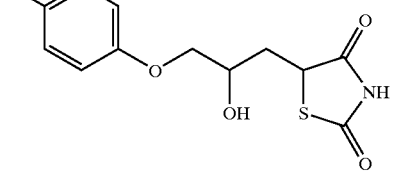 | 96–98 | 50.52 4.24 4.91 | 50.35 4.35 4.79 | E |

TABLE II-continued

| Compound | STRUCTURE | m.p. in °C. (Köfler) | calculated C H N | found C H N 0.5 H$_2$O | Route of synthesis |
|---|---|---|---|---|---|
| 18 | (structure) | 134–136 | 56.92 5.87 5.10 | 56.89 5.88 5.11 | A |
| 19 | (structure) | 106–108 | 57.35 5.21 5.57 | 57.18 5.24 5.56 | F |
| 20 | (structure) | 101–103 | 56.93 5.80 4.74 | 56.85 5.82 4.73 | A |
| 21 | (structure) | 234–236 | 51.24 3.94 4.98 | 51.12 4.02 4.87 | C |

EXAMPLE IX 100 mg 5-[3-(4-fluorophenoxy)propyl]-2,4-thiazolidinedione tablets

| | |
|---|---|
| Active ingredient | 100 g |
| Wheat starch | 45 g |
| Maize starch | 55 g |
| Microcrystalline cellulose | 12 g |
| Ethyl cellulose | 8 g |
| Magnesium stearate | 5 g | for 1000 finished tablets with an average weight of 0.225 g

EXAMPLE X 50 mg 5-(2-phenoxyethyl)-2,4-thiazolidinedione gelatin capsules

| | |
|---|---|
| Active ingredient | 50 g |
| Lactose | 75 g |
| Magnesium stearate | 5 g | for 1000 finished gelatin capsules with an average weight of 0.130 g

EXAMPLE XI 75 mg 5-[2-(2-naphthoxy)ethyl]2,4-thiazolidinedione coated tablets

| | |
|---|---|
| Active ingredient | 75 g |
| Silica | 39 g |
| Lactose | 112 g |
| Carboxymethyl starch as sodium salt | 9 g |
| Talc | 8 g |
| Magnesium stearate | 7 g | for 1000 centres weighing on average 250 g

Coating

Lac

Gelatin

Gum arabic

Sucrose

Titanium dioxide

Beeswax

Carnauba wax

Ethyl vanilin for 1000 finished coated tablets with an average weight of 0.400 g.

What is claimed is:

1. A pharmacologically acceptable basic salt of 5-phenoxyalkyl 2,4-thiazolidinediones of general formula I:

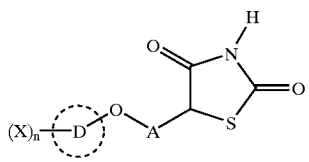

in which:
   A represents an ethylene group;
   D represents a homo- or heterocarbon mono-, di or tricyclic aromatic structure which may include one or more heteroatoms;
having from 1 to 6 carbon atoms, an alkoxy group having from 1 to 6 carbon atoms, an alkoxyalkyl group in which the alkoxy and alkyl groups are defined as above, an aryl group defined as an aromatic cyclic structure comprising one or two rings optionally including one or two heteroatoms in the ring, an aralkyl group in which the alkyl group is defined as above and the aryl group is defined as above and optionally comprises one or more substituents, an aralkylaryl group in which the aralkyl and aryl groups are defined as above, a halogen, a trifluoromethyl, a cyano, a hydroxyl, a nitro, an amino, a carboxyl, an alkosycarbonyl, a carboxamide, a sulfonyl, a sulfone, a sulfonamide, a sulfamoyl, an alkylsulfonylamino, an acylamino, a trifluoromethoxy;
   n is an integer ranging from 1 to 3.

2. A solvate with water and an organic solvent of the compound of general formula I according to claim 1.

3. A compound according to claim 1, wherein the compound is a pharmacologically acceptable salt of:
5-(2-phenoxyethyl)-2,4-thiazolidinedione
5-[2-(4-fluorophenoxy)ethyl]-2,4-thiazolidinedione
3-{[1-hydroxy-2-(4-fluorophenoxy)]ethyl}-2,4-thiazolidinedione
5-[1-methyl-2-phenoxyethyl]-2,4-thiazolidinedione
5-[2-(4-cyanophenoxy)ethyl]-2,4-thiazolidinedione
5-[2-(2-fluorophenoxy)ethyl]-2,4-thiazolidinedione or
5-[2-(2-naphthyloxy)ethyl]-2,4-thiazolidinedione.

4. A method of treating the metabolic syndrome of insulin resistance, by administrating an effective amount of the compound according to claim 1.

5. A compound chosen from
5-[3-(4-fluorophenoxy)propyl]-2,4-thiazolidinedione
5-(2-phenoxyethyl)-2,4-thiazolidinedione
5-[2-(4-fluorophenoxy)ethyl]-2,4-thiazolidinedione
5-{[1-hydroxy-2-(4-fluorophenoxy)]ethyl}-2,4-thiazolidinedione
5-{[2-hydroxy-3-(4-fluorophenoxy)]propyl}-2,4-thiazolidinedione
5-[1-methyl-2-phenoxyethyl]-2,4-thiazolidinedione
5-[2-(4-cyanophenoxy)ethyl]-2,4-thiazolidinedione
5-[2-(2-fluorophenoxy)ethyl]-2,4-thiazolidinedione or
5-[2-(2-naphthyloxy)ethyl]-2,4-thiazolidinedione
and their pharmacologically acceptable salts.

6. An enantiomer of the compound according to claim 5.

7. A pharmacologically acceptable basic salt of the compound according to claim 5.

8. The compound of claim 5, wherein the compound is 5-[2-(4-cyanophenoxy)ethyl]-2,4-thiazolidinedione.

9. A method of treating the metabolic syndrome of insulin resistance, by administrating an effective amount of the compound according to claim 5.

10. The compound of claim 5, wherein the compound is 5-(2-phenoxyethyl)-2,4-thiazolidinedione.

11. A pharmaceutical composition comprising, as active ingredient, at least one compound of claim 5.

12. A pharmaceutical composition according to claim 11, wherein the vehicle or excipient is one of those which are suitable for administration by the parenteral, digestive, rectal, permucosal or percutaneous route.

13. Pharmaceutical composition according to claim 11, wherein the active ingredient content is from 1 to 200 mg per unit dose.

14. An injectable solution, suspension or multi-dose vial, a plain or coated tablet, a capsule, a pill, a cachet, a powder or a suppository comprising the pharmaceutical composition according to claim 11.

15. An excipient of a cellulose derivative, a microcrystalline cellulose, an alkaline-earth metal carbonate, a magnesium phosphate, a starch, a modified starch, a lactose, a cocoa butter, a polyethyleneglycol sterate, water, an aqueous solution, a physiological saline or a isotonic solution incorporating the pharmaceutical composition according to claim 11.

16. An enantiomer or a solvate of a 5-phenoxyalkyl-2,4-thiazolidinedione of formula I:

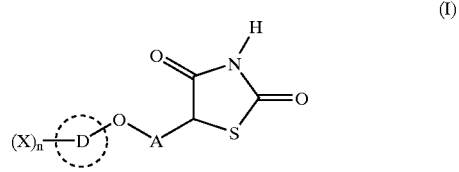

in which:
   A represents an ethylene group;
   D represents a homo- or heterocarbon mono-, di- or tricyclic aromatic structure which may include one or more heteroatoms;
   X represents a substituent of the aromatic structure, chosen from hydrogen, an alkyl group having from 1 to 6 carbon atoms, an alkoxy group having from 1 to 6 carbon atoms, an alkoxyalkyl group in which the alkoxy and alkyl groups are defined as above, an aryl group defined as an aromatic cyclic structure comprising one or two rings optionally including one or two heteroatoms in the ring, an aralkyl group in which the alkyl group is defined as above and the aryl group is defined as above and optionally comprises one or more substituents, an aralkylaryl group in which the aralkyl and aryl groups are defined as above, a halogen, a trifluoromethyl, a cyano, a hydroxyl, a nitro, an amino, a carboxyl, an alkoxycarbonyl, a carboxamide, a sulfonyl, a sulfone, a sulfonamide, a sulfamoyl, an alkylsulfonylamino, an acylamino, a trifluoromethoxy;
   n is an integer ranging from 1 to 3.

17. A method of treating the metabolic syndrome of insulin resistance, by administrating an effective amount of the compound according to claim 16.

18. A pharmacologically acceptable salt chosen from:
5-[3-(4-fluorophenoxy)propyl]-2,4-thiazolidinedione or
5-{[2-hydroxy-3-(4-fluorophenoxy)]propyl}-2,4-thiazolidinedione.

* * * * *